United States Patent [19]
Ohmura et al.

[11] Patent Number: 5,976,229
[45] Date of Patent: Nov. 2, 1999

[54] UNDERWATER ANTI-FOULING AGENT AND ANTI-FOULING PAINT CONTAINING THE UNDERWATER ANTI-FOULING AGENT

[75] Inventors: Yutaka Ohmura, deceased, late of Kitakanbara-gun, by Toshiko Ohmura, legal representative; Ken Ohkura, Tokyo, both of Japan

[73] Assignees: Kyosei Chemicals Co., Ltd.; Dainichiseika Color & Chemicals Mfg. Co., Ltd., both of Tokyo, Japan

[21] Appl. No.: 09/127,811

[22] Filed: Aug. 3, 1998

[30] Foreign Application Priority Data

Jan. 28, 1998 [JP] Japan .................................. 10-016079

[51] Int. Cl.$^6$ ..................................................... C09D 5/16
[52] U.S. Cl. ..................................... 106/18.32; 106/15.05; 424/78.09; 424/635; 424/646; 523/122; 523/177
[58] Field of Search .............................. 106/18.32, 15.05; 424/78.09, 635, 646; 523/122, 177

[56] References Cited

U.S. PATENT DOCUMENTS 4,130,432 12/1978 Wehner et al. ....................... 106/18.31
4,698,098 10/1987 Gansloser et al. ................... 106/18.36

OTHER PUBLICATIONS

WPIDS Abstract No 83–845561, abstract of German Patent Specification No. 3,222,090 (Dec. 1983).

*Primary Examiner*—Anthony Green
*Attorney, Agent, or Firm*—Oblon, Spivak, McClelland, Maier & Neustadt, P.C.

[57] ABSTRACT

An underwater anti-fouling agent contains as an effective component a hexacyano compound, preferably a hexacyanoferrate. The anti-fouling agent is useful for the preparation of an anti-fouling paint.

20 Claims, No Drawings

5,976,229

UNDERWATER ANTI-FOULING AGENT AND ANTI-FOULING PAINT CONTAINING THE UNDERWATER ANTI-FOULING AGENT

BACKGROUND OF THE INVENTION a) Field of the Invention

This invention relates to an underwater anti-fouling agent effective in preventing aquatic organisms such as algae, barnacles and hard-shelled mussels from attaching themselves on objects maintained in contact with seawater, such as ships, ocean rigs and fish nets, and also to an anti-fouling paint making use of the underwater anti-fouling agent.

b) Description of the Related Art

In general, ships' bottoms, ocean rigs, fish nets, fish preserves and the like are maintained in contact with seawater for extended time. During these periods, submarine organisms such as algae, barnacles and hard-shelled mussels attach themselves on seawater-contacting surfaces of such objects, leading to problems such as lowered running speeds due to increases in weight and stream resistance in the case of ships and significantly shortened useful life in the case of fish nets and ocean rigs. Accordingly, a variety of methods have been applied to date for the prevention of attachment of submarine organisms. Known chemical or biochemical methods include, for example, use of materials on which the above submarine organisms are difficult to attach and use of repellents, anti-fouling agents and the like for submarine organisms, such as copper plates, silicone resin paints and fluorine-containing paints. Among such anti-fouling methods, it is the common practice to coat the above-mentioned ships and the like with anti-fouling paints containing anti-fouling agents, because inter alia this coating method is applicable in a wide range of fields, can bring about high effects and can be easily applied. Anti-fouling paints have been available conventionally, each of which is formed of a binder component—which is composed of a seawater-insoluble polymer such as an acrylic resin, alkyd resin or chlorinated rubber and rosin—and an anti-fouling agent such as an organotin compound, organotin polymer or copper suboxide added therein.

A paint with an organotin compound or organotin polymer contained therein is designed in such a way that the organotin compound or organotin polymer in the paint is gradually eluted into water or the paint containing the organotin compound or organotin polymer therein is scraped off little by little to spread in water and always to expose a new paint surface. Despite its high preventive effects against the attachment of underwater organisms, it is accompanied by problems from the standpoint of safety and sanitation and also environmental preservation in that the organotin compound or organotin polymer is eluted into water.

SUMMARY OF THE INVENTION

An object of the present invention is to eliminate the above-described current problems; and therefore to provide an underwater anti-fouling agent, which prevents over an extended period of time various submarine organisms such as barnacles and hard-shelled mussels from gradually attaching themselves on surfaces of seawater-contacting parts of ships, ocean rigs and fishing nets, and is also excellent in safety and sanitation and environmental preservation, and also an anti-fouling paint containing the underwater anti-fouling agent.

In one aspect of the present invention, there is thus provided an underwater anti-fouling agent comprising a hexacyano compound as an effective component or a hexacyano compound and copper suboxide as effective components. In another aspect of the present invention, there is also provided an anti-fouling paint comprising a paint component and the underwater anti-fouling agent.

From the standpoint of organism attachment preventiveness and anti-elution property, the hexacyano compound may preferably be a hexacyanoferrate in the present invention.

The underwater anti-fouling agent according to the present invention does not promote gelation in paint formulations and hence provide the paint formulations with excellent storage stability. Further, the anti-fouling paint available from the underwater anti-fouling agent of this invention exhibits superb anti-fouling properties over an extended period of time. Owing to the use of the hexacyano compound which remains stable in water, the underwater anti-fouling agent can retain its preventive effects against the attachment of animals and plants, which live or grow in the seawater and the like, over an extended period of time without developing substantial problems in safety and sanitation and environmental preservation.

DETAILED DESCRIPTION OF THE INVENTION AND PREFERRED EMBODIMENTS

The present invention will hereinafter be described in more detail on the basis of certain preferred embodiments.

The underwater anti-fouling agent according to the present invention is generally used in a form dispersed in a resin capable of forming a coating film such as an acrylic resin, chlorinated rubber of vinyl resin, although it may be used directly as is.

It is particularly useful to add the underwater anti-fouling agent of this invention to a suitable paint formulation and then to use it under submerged conditions like an anti-fouling paint for large ships and ocean rigs. Namely, the hexacyano compound can be used as a ship bottom paint or an anti-fouling paint for fishery facilities by dissolving or dispersing it in a coating-film-forming component and hence converting it into a paint form.

Examples of the hexacyano compound employed in the present invention can include potassium hexacyanochromate (III), potassium hexacyanocobaltate (III), ammonium hexacyanoferrate (II), ammonium hexacyanoferrate (III), potassium hexacyanoferrate (II), potassium hexacyanoferrate (III), sodium hexacyanoferrate (II), sodium hexacyanoferrate (III), potassium sodium hexacyanoferrate (II), iron hexacyanoferrate (II), copper hexacyanoferrate (II), iron hexacyanoferrate (III), and sodium hexacyanomanganate (II). From the standpoint of safety and sanitation and environmental preservation, however, at least one hexacyanoferrate selected from the sodium salt, potassium salt or ammonium salt or a mixed salt thereof of iron (II) hexacyanoferrate (II), iron (II) hexacyanoferrate (III), iron (III) hexacyanoferrate (II) or iron (III) hexacyanoferrate (III) is preferred.

The underwater anti-fouling agent according to the present invention may comprise only one of the above-described hexacyano compounds or a mixture of two or more of them. As a further alternative, a combination of one or more of these hexacyano compounds and copper suboxide can also be used effectively. Copper suboxide usable in the present invention can also be called "cuprous oxide" and is in the form of red powder, and has been used widely for many years as ship bottom paints and also for the anti-fouling of fishing nets and the like. The proportion of copper suboxide, which is used in combination with the hexacyano compound, may preferably be in a range of from 1 to 10,000 parts by weight per 100 parts by weight of the hexacyano compound.

Illustrative of the coating-film-forming resin for use in the anti-fouling paint of the present invention can be acrylic resins, epoxy resins, polyester resins, epoxy resins, butyral resins, vinyl resins, polyurethane resins, urea resins, and ethylene-vinyl acetate resins.

Concerning the proportion of the hexacyano compound or the total proportion of the hexacyano compound and copper suboxide in the anti-fouling paint of this invention, the hexacyano compound or the hexacyano compound and copper suboxide are added in an proportion of 2 to 80 wt. %, preferably 5 to 60 wt. % based on the solid content of the coating-film-forming resin in the anti-fouling paint. A proportion smaller than 2 wt. % cannot bring about sufficient organism attachment preventiveness, while a proportion greater than 80 wt. % may results in a coating film with deteriorated physical properties. Proportions outside the above range are not preferred.

To formulate the anti-fouling paint of this invention, the coating-film-forming resin is dissolved or dispersed in water, methanol, ethanol, propanol, isopropanol, butanol, ethyl acetate, butyl acetate, methyl ethyl ketone, acetone, xylene, toluene, ethyl cellosolve or the like, adding the hexacyano compound to the resultant solution or dispersion and further adding a dispersant, a hardening agent, a hardening promoter and/or the like as needed.

The present invention will next be described specifically on the basis of the following Experiments, Examples and Comparative Examples.

EXPERIMENTS

Preparation of Underwater Anti-fouling Agents (Hexacyano Compounds)

Example 1

Into a 3,000-ml beaker fitted with a stirrer and a thermometer, 500 ml of water, 60 g of sulfuric acid, 44 g of ammonium sulfate and 100 g of ferrous sulfate heptahydrate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 160 g of sodium ferrocyanate decahydrate were dissolved. The resulting solution was heated to 80° C.

While stirring the solution of ferrous sulfate, the solution of sodium ferrocyanate was then poured into the solution of ferrous sulfate in the course of 10 minutes. Subsequent to the completion of the pouring, the resulting mixture was heated to 95 to 98° C. and was maintained at the same temperature for 1 hour. A solution of 6.4 g of sodium chlorate in 50 ml of water was then added to the mixture, followed by continuous stirring for 1 hour. After 400 ml of chilled water were added to the reaction mixture, the resulting mixture was filtered. The thus-obtained filter cake was washed three times with 2,000 ml of water. The filter cake was dried at 60° C. for 16 hours and was then ground, whereby an underwater anti-fouling agent A was obtained.

Experiment 2

Into a 3,000-ml beaker fitted with a stirrer and a thermometer, 500 ml of water, 60 g of sulfuric acid and 100 g of ferrous sulfate heptahydrate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 115 g of potassium ferrocyanate trihydrate were dissolved. The resulting solution was heated to 80° C.

While stirring the solution of ferrous sulfate, the solution of potassium ferrocyanate was then poured into the solution of ferrous sulfate in the course of 10 minutes. Subsequent to the completion of the pouring, the resulting mixture was heated to 95 to 98° C. and was maintained at the same temperature for 1 hour. A solution of 6.4 g of sodium chlorate in 50 ml of water was then added to the mixture, followed by continuous stirring for 1 hour. After 400 ml of chilled water were added to the reaction mixture, the resulting mixture was filtered. The thus-obtained filter cake was washed three times with 2,000 ml of water. The filter cake was dried at 60° C. for 16 hours and was then ground, whereby an underwater anti-fouling agent B was obtained.

Experiment 3

Into a 3,000-ml beaker fitted with a stirrer and a thermometer, 500 ml of water, 60 g of sulfuric acid, 44 g of ammonium sulfate and 58 g of copper sulfate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 160 g of sodium ferrocyanate decahydrate were dissolved. The resulting solution was heated to 80° C.

While stirring the solution of ferrous sulfate, the solution of sodium ferrocyanate was then poured into the solution of ferrous sulfate in the course of 10 minutes. Subsequent to the completion of the pouring, the resulting mixture was heated to 95 to 98° C. and was maintained at the same temperature for 1 hour. After 400 ml of chilled water were added to the reaction mixture, the resulting mixture was filtered. The thus-obtained filter cake was washed three times with 2,000 ml of water. The filter cake was dried at 60° C. for 16 hours and was then ground, whereby an underwater anti-fouling agent C was obtained.

Experiment 4

Into a 3,000-ml beaker fitted with a stirrer and a thermometer, 500 ml of water, 60 g of sulfuric acid, 44 g of ammonium sulfate and 100 g of ferrous sulfate heptahydrate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 160 g of sodium ferrocyanate decahydrate were dissolved. The resulting solution was heated to 80° C.

While stirring the solution of ferrous sulfate, the solution of sodium ferrocyanate was then poured into the solution of ferrous sulfate in the course of 10 minutes. Subsequent to the completion of the pouring, the resulting mixture was heated to 95 to 98° C. and was maintained at the same temperature for 1 hour. After 400 ml of chilled water were added to the reaction mixture, the resulting mixture was filtered. The thus-obtained filter cake was washed three times with 2,000 ml of water. The filter cake was dried at 60° C. for 16 hours and was then ground, whereby an underwater anti-fouling agent D was obtained.

Experiment 5

Into a 3,000-ml beaker fitted with a stirrer and a thermometer, 500 ml of water, 60 g of sulfuric acid, 44 g of ammonium sulfate and 100 g of ferrous sulfate heptahydrate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 160 g of sodium ferrocyanate decahydrate were dissolved. The resulting solution was heated to 80° C.

While stirring the solution of ferrous sulfate, the solution of sodium ferrocyanate was then poured into the solution of ferrous sulfate in the course of 10 minutes. Subsequent to the completion of the pouring, the resulting mixture was heated to 95 to 98° C. and was maintained at the same temperature for 1 hour. To the reaction mixture, a solution of 6.4 g of sodium chlorate in 50 ml of water was then added, followed by continuous stirring for 1 hour. After 400 ml of chilled water were added to the reaction mixture, the resulting mixture was filtered. The thus-obtained filter cake was washed three times with 2,000 ml of water. Triethylenetetramine (6 g) was added to the filter cake, and the resulting mixture was agitated together with 50 ml of water for 10 minutes in a juicer. The thus-obtained mixture was dried at 60° C. for 16 hours and was then ground, whereby an underwater anti-fouling agent E was obtained.

Experiment 6

Into a 3,000-ml beaker fitted with a stirrer and a thermometer, 500 ml of water, 60 g of sulfuric acid, 44 g of ammonium sulfate and 100 g of ferrous sulfate heptahydrate were added, and the contents were stirred into a solution. Water was added further to adjust the volume of the reaction mixture to 1,200 ml. The reaction mixture was then heated to 90° C. On the side, 600 ml of water were placed in a 1,000-ml beaker furnished additionally, in which 160 g of sodium ferrocyanate decahydrate were dissolved. The resulting solution was heated to 80° C.

While stirring the solution of ferrous sulfate, the solution of sodium ferrocyanate was then poured into the solution of ferrous sulfate in the course of 10 minutes. Subsequent to the completion of the pouring, the resulting mixture was heated to 95 to 98° C. and was maintained at the same temperature for 1 hour. After 400 ml of chilled water were added to the reaction mixture, the resulting mixture was filtered. The thus-obtained filter cake was washed three times with 2,000 ml of water. Triethylenetetramine (6 g) was added to the filter cake, and the resulting mixture was agitated together with 50 ml of water for 10 minutes in a juicer. The thus-obtained mixture was dried at 60° C. for 16 hours and was then ground, whereby an underwater anti-fouling agent F was obtained.

Experiment 7

An underwater anti-fouling agent G was obtained by adding 100 g of copper suboxide to 100 g of the underwater anti-fouling agent C obtained in Experiment 3.

Organism Attachment Preventiveness Evaluation Tests

Examples 1–7

In each Example, 3.0 g of one of the underwater anti-fouling agents A–G, which had been obtained in the experiment of the corresponding number out of Experiment 1 to Experiment 7, were added to a mixture consisting of 9.0 g of a phthalic acid resin varnish ("J-557 Varnish", trade name; product of Dainippon Ink & Chemicals, Incorporated), 4.5 g of mineral terpene and 52.5 g of glass beads (3 mm in diameter). The resultant mixture was placed in a stopper-equipped, polyethylene-made 100-ml sample bottle and was then stirred for 60 minutes on a paint shaker. The same phthalic acid resin varnish (51.0 g) was then added, followed by stirring for 5 minutes on the paint shaker.

To the thus-obtained coating formulation, 0.42 g of a drier (which consisted of 50 parts by weight of cobalt naphthenate, 27 parts by weight of lead naphthenate and 23 parts by weight of xylene) was added, followed by stirring. Coating formulations obtained as described above were brush-painted on sandblasted iron plates of 300 mm×200 mm×3.2 mm, respectively.

After the iron plates were dried overnight at the surrounding temperature, the same coating formulations were brush-painted on the respective coating films. The thus-painted iron plates were then dried overnight at the surrounding temperature, whereby test pieces were prepared.

Comparative Example 1

Test pieces were prepared in the same manner as in Examples 1–7 except that the coating formulations were used without the underwater anti-fouling agents.

Comparative Example 2

Test pieces were prepared in the same manner as in Examples 1–7 except that copper suboxide (3.0 g) was used instead of the respective underwater anti-fouling agents.

Evaluation

The test pieces obtained in Examples and Comparative Examples were fixed on 600 mm×1100 mm frames made of ¾B stainless pipes at the rate of 4 test pieces per frame. The test pieces were immersed in seawater of about 10 to 20° C., and upon elapsed time of 1 month, 3 month and 6 month, the extent of attachment of barnacles, slime, algae and the like was observed. The results are presented in Table 1.

TABLE 1

|  | Underwater anti-fouling agent | 1 month later | 3 months later | 6 months later |
| --- | --- | --- | --- | --- |
| Example 1 | A | No organism attached. | Slime attached slightly. | Algae and barnacles attached slightly. |
| Example 2 | B | No organism attached. | Slime attached slightly. slightly. | Algae and barnacles attached |

TABLE 1-continued

|  | Underwater anti-fouling agent | 1 month later | 3 months later | 6 months later |
|---|---|---|---|---|
| Example 3 | C | No organism attached. | Slime attached slightly. | Algae and barnacles attached slightly. |
| Example 4 | D | No organism attached. | No organism attached. | Algae attached. |
| Example 5 | E | No organisin attached. | No organism attached. | Algae attached. |
| Example 6 | F | No organism attached. | No organism attached. | Algae attached. |
| Example 7 | G | No organism attached. | No organism attached. | Algae attached. |
| Comp. Ex. 1 | None | Algae and barnacles attached slightly. | Many algae and barnacles attached densely. | Barnacles attached considerably. |
| Comp. Ex. 2 | Copper suboxide alone | Slime attached slightly. | Slime attached thickly. | Algae and barnacles attached. |

Example 8

In 100 g of a solution of 65 parts by weight of rosin, 25 parts by weight of linseed oil and 10 parts by weight of linseed fatty acids in 100 parts by weight of mineral spirit, 30 g of the underwater anti-fouling agent E, 25 g of red iron oxide, 2 g of manganese naphthenate and 2 g of lead naphthenate were mixed. The resultant mixture was then dispersed for 20 minutes in a batch attritor, whereby ship bottom paint No. 2 was formulated. The ship bottom paint No. 2 was brush-pained on a sandblasted iron plate which had been coated beforehand with a commercial ship bottom rust preventive paint. The iron plate was dried for 5 days at the surrounding temperature, whereby a test piece was prepared.

Example 9

Another test piece was prepared in a similar manner as in Example 8 except for the use of the underwater anti-fouling agent F in place of the underwater anti-fouling agent E.

Comparative Example 3

A further test piece was prepared in a similar manner as in Example 8 except for the use of 30 g of copper suboxide in place of the underwater anti-fouling agent E.

Example 10

Combined were 12 parts by weight of linseed oil, 12 parts by weight of tung oil, 32 parts by weight of an ester gum, 40 parts by weight of red iron oxide, 20 parts by weight of creosote oil, 40 parts by weight of the underwater anti-fouling agent F, 42 parts by weight of mineral spirit, and 2 parts by weight of the same drier as that used in Examples 1–7. The resulting mixture was dispersed for 20 minutes in a batch attritor, whereby a wooden ship bottom paint was formulated.

A piece (200 mm×200 mm×10 mm) of a pine tree board, which had been fully dried and furnished separately, was polished at the entire surface thereof and was then brush-painted with the wooden ship bottom paint. After the board piece was dried for 24 hours, the board piece was additionally brush-painted twice and was then dried for 7 days at the surrounding temperature, whereby a still further test piece was prepared.

Example 11

A still further test piece was prepared in the same manner as in Example 10 except that the underwater anti-fouling agent G was used in place of the underwater anti-fouling agent F.

Comparative Example 4

A still further test piece was prepared in the same manner as in Example 10 except for the exclusion of the underwater anti-fouling agent F from the composition.

Evaluation

The test pieces, which had been obtained in Example 8, Example 9, Comparative Example 3, Example 10, Example 11 and Comparative Example 4, respectively, were fixed on a frame and were then immersed in seawater of about 20 to 25° C., and upon elapsed time of 30 days, 90 days and 180 days, the extent of attachment of barnacles, slime, algae and the like was observed. The results are presented in Table 2.

This application claims the priority of Japanese Patent Application No. HEI 10-16079 filed Jan. 28, 1998, which is incorporated herein by reference.

TABLE 2

|  | Underwater anti-fouling agent | 1 month later | 3 months later | 6 months later |
|---|---|---|---|---|
| Example 8 | E | No organism attached. | Slime attached slightly. | Algae and barnacles attached slightly. |
| Example 9 | F | No organism | No | Algae and barna- |

TABLE 2-continued

|  | Underwater anti-fouling agent | 1 month later | 3 months later | 6 months later |
|---|---|---|---|---|
|  |  | attached. | organism attached. | cles attached slightly. |
| Comp. Ex. 3 | Copper suboxide | No organism attached. | Slime attached. abundantly. | Algae and barnacles attached |
| Example 10 | F | No organism attached. | Slime attached slightly. | Algae and barnacles attached slightly. |
| Example 11 | G | No organism attached. | No organism attached. | Algae attached. slightly |
| Comp. Ex. 4 | None | Algae and barnacles attached slightly. | Algae and barnacles attached. | Algae and barnacles attached abundantly. |

What is claimed is:

1. An underwater anti-fouling agent, comprising:
   100 parts by weight of at least one hexacyano compound, and
   1 to 10,000 parts by weight of cuprous oxide.

2. The underwater anti-fouling agent of claim 1, wherein said hexacyano compound is a hexacyanoferrate.

3. The underwater anti-fouling agent of claim 2, wherein said hexacyanoferrate comprises at least one member selected from the group consisting of sodium hexacyanoferrate, potassium hexacyanoferrate, ammonium hexacyanoferrate, iron (II) hexacyanoferrate (II), iron (II) hexacyanoferrate (III), iron (III) hexacyanoferrate (II) and iron (III) hexacyanoferrate (III).

4. An anti-fouling paint, comprising:
   the underwater anti-fouling agent of claim 1, and
   a resin,
   wherein said anti-fouling agent is present in an amount of 2 to 80 wt. % based on the solid content of said resin.

5. An anti-fouling paint, comprising:
   the underwater anti-fouling agent of claim 2, and
   a resin,
   wherein said anti-fouling agent is present in an amount of 2 to 80 wt. % based on the solid content of said resin.

6. An anti-fouling paint, comprising:
   the underwater anti-fouling agent of claim 3, and
   a resin,
   wherein said anti-fouling agent is present in an amount of 2 to 80 wt. % based on the solid content of said resin.

7. The anti-fouling paint of claim 4, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

8. The anti-fouling paint of claim 5, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

9. The anti-fouling paint of claim 6, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

10. An anti-fouling paint, comprising:
    the underwater anti-fouling agent of claim 1, and
    a resin,
    wherein said anti-fouling agent is present in an amount of 5 to 60 wt. % based on the solid content of said resin.

11. An anti-fouling paint, comprising:
    the underwater anti-fouling agent of claim 1, and
    a resin,
    wherein said anti-fouling agent is present in an amount of 5 to 60 wt. % based on the solid content of said resin.

12. An anti-fouling paint, comprising:
    the underwater anti-fouling agent of claim 3, and
    a resin,
    wherein said anti-fouling agent is present in an amount of 5 to 60 wt. % based on the solid content of said resin.

13. The anti-fouling paint of claim 10, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

14. The anti-fouling paint of claim 11, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

15. The anti-fouling paint of claim 12, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

16. The anti-fouling paint of claim 7, wherein said resin is selected from the group consisting of an acrylic resin, a vinyl chloride-vinyl acetate copolymer, an ethylene-vinyl acetate copolymer, an epoxy resin, a vinyl chloride resin, a polyurethane resin, a silicon resin, a styrene resin or a polyester resin.

17. A method of making an anti-fouling paint, comprising:
    dissolving or dispersing the anti-fouling agent of claim 1 into a solution or dispersion of a resin.

18. A method of making an anti-fouling paint, comprising:
    dissolving or dispersing the anti-fouling agent of claim 3 into a solution or dispersion of a resin.

19. The method of claim 17, further comprising adding a dispersant, a hardening agent, or a hardening promoter.

20. The method of claim 17, wherein said resin is selected from the group consisting of acrylic resins, epoxy resins, polyester resins, butyral resins, vinyl resins, polyurethane resins, urea resins, ethylene-vinyl acetate resins, silicon resins, and styrene resins.

* * * * *

UNITED STATES PATENT AND TRADEMARK OFFICE
CERTIFICATE OF CORRECTION

PATENT NO. : 5,976,229

DATED : November 2, 1999

INVENTOR(S): Yutaka OHMURA, et al

It is certified that an error appears in the above-identified patent and that said Letters Patent is hereby corrected as shown below:

On the title page, item [73], the Assignee's name should read:

--[73] Assignees: Kyosei Chemical Co., Ltd:
Dainichiseika Color & Chemicals
Mfg. Co., Ltd. both of Tokyo, Japan Signed and Sealed this Twenty-fifth Day of July, 2000

Attest:

Q. TODD DICKINSON

*Attesting Officer*   *Director of Patents and Trademarks*